(12) United States Patent
Lee et al.

(10) Patent No.: US 8,715,976 B2
(45) Date of Patent: May 6, 2014

(54) RECOMBINANT MICROORGANISMS HAVING ENHANCED PROPANOL AND METHOD FOR PREPARING PROPANOL USING THE SAME

(75) Inventors: Sang Yup Lee, Daejeon (KR); Yong Jun Choi, Daejeon (KR); Jin Hwan Park, Daejeon (KR)

(73) Assignee: Korea Advanced Institute of Science and Technology, Daejeon (KR)

( * ) Notice: Subject to any disclaimer, the term of this patent is extended or adjusted under 35 U.S.C. 154(b) by 0 days.

(21) Appl. No.: 13/537,988

(22) Filed: Jun. 29, 2012

(65) Prior Publication Data

US 2013/0164805 A1 Jun. 27, 2013

(30) Foreign Application Priority Data

Jun. 29, 2011 (KR) ........................ 10-2011-0064088

(51) Int. Cl.
*C12P 7/04* (2006.01)
(52) U.S. Cl.
USPC .......................................................... 435/157
(58) Field of Classification Search
USPC ............................. 435/157, 69.1, 252.3, 23.2
See application file for complete search history.

(56) References Cited

PUBLICATIONS

Atsumi et al., "Non-fermentative pathways for synthesis of branched-chain higher alcohols as biofuels", Nature, vol. 451: 3, 86-90. Jan. 2008.*
Suzuki, Nobuaki, et al.; "New Multiple-Deletion Method for the *Corynebacterium glutamicum* Genome, Using a Mutant lox Sequence," Applied and Environmental Microbiology, 2005, pp. 8472-8480, vol. 71.
Atsumi, Shota, et al.; "Directed Evolution of *Methanococcus jannaschii* Citramalate Synthase for Biosynthesis of 1-Propanol and 1-Butanol by *Escherichia coli*," Applied and Environmental Microbiology, 2008, pp. 7802-7808, vol. 74.
Ulrich Güldener, et al.; "A new efficient gene disruption cassette for repeated use in budding yeast," Nucleic Acids Research, 1996, pp. 2519-2524, vol. 24.
Holland-Staley, Carol, et al.; "Aerobic Activity of *Escherichia coli* Alcohol Dehydrogenase Is Determined by a Single Amino Acid," Journal of Bacteriology, 2000, pp. 6049-6054, vol. 182.
Lee, P.C., et al,; "Batch and continuous cultivation of *Anerobiospirillum succiniciproducens* for the production of succinic acid from whey," Applied Microbiology Biotechnology, 2000, pp. 23-27, vol. 54.

Lee, P.C., et al.; "Succinic Acid Production with Reduced By-Product Formation in the Fermentation of *Anaerobiospirillum succiniciproducens* Using Glycerol as a Carbon Source," Biotechnology and Bioengineering, 2001, pp. 41-48, vol. 72.
Lee, P.C., et al.; "Isolation and characterization of a new succinic acid-producing bacterium, *Mannheimia succiniciproducens* MBEL55E, from bovine rumen," Applied Microbiology Biotechnology, 2002, pp. 663-668, vol. 58.
Lee, P.C., et al.; "Batch and continuous cultures of *Mannheimia succiniciproducens* BMEL55E for the production of succinic acid from whey and corn steep liquor," Bioprocess Biosyst Eng, 2003, pp. 63-67, vol. 26.
Lee, P.C., et al.; "Biological conversion of wood hydrolysate to succinic acid by *Anaerobiospirillum succiniciproducens*," Biotechnology Letters, 2003, pp. 111-114, vol. 25.
Lee, Jin-Ho, et al.; "Global Analyses of Transcriptomes and Proteomes of a Parent Strain and an L-Threonine-Overproducing Mutant Strain," Journal of Bacteriology, 2003, pp. 5442-5451, vol. 185.
Lee, Sang Yup, et al.; "Fermentative Butanol Production by Clostridia," Biotechnology and Bioengineering, 2008, pp. 209-228, vol. 101.
Nagy, Andras, et al.; "Cre Recombinase: The Universal Reagent for Genome Tailoring," Genesis, 2000, pp. 99-109, vol. 26.
Sambrook, E.F., et al.; "Molecular Cloning: a laboratory manual," 1987, Second Edition, Reference Cover Page.
Hiszczyńska-Sawicka, Elżbieta, et al.; "Effect of *Escherichia coli* IHF Mutations on Plasmid p15A Copy Number," Plasmid, 1997, pp. 174-179, vol. 38.
Datsenko, Kirill A., et al.; "One-step inactivation of chromosomal genes in *Escherichia coli* K-12 using PCR products," PNAS, 2000, pp. 6640-6645, vol. 97.
Jäger, W., et al.; "Expression of the *Bacillus subtilis* sacB Gene Leads to Sucrose Sensitivity in the Gram-Positive Bacterium *Corynebacterium glutamicum* but Not in *Streptomyces lividans*," Journal of Bacteriology, 1992, pp. 5462-5465, vol. 174.
Qian, Zhi-Gang, et al.; "Metabolic Engineering of *Escherichia coli* for the Production of Putrescine: A four Caron Diamine," Biotechnology and Bioengineering, 2009, pp. 651-662, vol. 104.

* cited by examiner

*Primary Examiner* — Tekchand Saidha
*Assistant Examiner* — Rama P Ramanujam
(74) *Attorney, Agent, or Firm* — Tristan A. Fuierer; Andrew D. Gerschutz; Moore & Van Allen, PLLC

(57) ABSTRACT

The present invention relates to mutant microorganisms having the ability to produce propanol in high concentration and high yield, and to a method of producing propanol using the same. More particularly, the invention relates to mutant microorganisms having the ability to produce propanol in high concentration and high yield, which have introduced therein genes that encodes enzymes which are involved in the biosynthesis of propanol from threonine, and to a method of producing propanol using the same.

9 Claims, 6 Drawing Sheets

RECOMBINANT MICROORGANISMS HAVING ENHANCED PROPANOL AND METHOD FOR PREPARING PROPANOL USING THE SAME

CROSS-REFERENCE TO RELATED APPLICATIONS

This application is filed under the provisions of 35 U.S.C. §111(a) and claims the priority under 35 U.S.C. §119(a) of Korean Patent Application No. 10-2011-0064088 filed on 29 Jun. 2011, which is hereby incorporated by reference herein in its entirety.

BACKGROUND OF THE INVENTION

1. Field of the Invention

The present invention relates to mutant microorganisms having the ability to produce propanol in high concentration and high yield, and to a method of producing propanol using the same. More particularly, the present invention relates to mutant microorganisms having the ability to produce propanol in high concentration and high yield, which have introduced therein genes that encodes enzymes which are involved in the biosynthesis of propanol from threonine, and to a method of producing propanol using the same.

2. Background of the Related Art

Due to high oil prices and environmental concerns, the microbial production of biodiesel is attracting a great deal of attention. As biodiesel has been considered as an alternative fuel, which can substitute for diesel oil or used in a mixture with diesel oil in diesel engines, the market size thereof has increased rapidly. In the European Union (EU) in 2008, biodiesel was produced in an amount of 660 million tons and reached a market size of 5.5 billion euro.

In recent years, as propanol has been considered as an alternative fuel for gasoline, the market size thereof has increased rapidly. Currently, 10 to 12 billion pounds of propanol are being produced annually in the world (Lee, S. Y. et al., Biotechnology and Bioengineering 101: 209, 2008). Particularly, biopropanol has properties suitable as fuels, including suitable energy density, controllable volatility, sufficient octane number, low impurity content and the like, and it has advantages over ethanol in that it has higher energy efficiency, is more easily mixed with gasoline and can be used in existing oil pipelines or automotive engines.

The production of 1 g/L of propanol in wild-type *E. coli* was reported (Atsumi, S. et al, Directed evolution of *Methanococcus jannaschii* citramalate synthase for biosynthesis of 1-propanol and 1-butanol by *Escherichia coli*. Appl Environ Microbiol, 74:7802-7808, 2008), but this amount of production is insufficient for industrial applications, and the activities of genes introduced into the strain are low and thus need to be further improved.

Therefore, it is believed that producing increased amounts of propanol using strains developed using metabolic engineering or omics technology is required to replace fossil fuels which are being exhausted.

Accordingly, the present inventors have made extensive efforts to increase the efficiency of production of propanol, and as a result, have identified genes that encode enzymes involved in the biosynthesis of propanol from threonine, and have constructed mutant microorganisms having introduced therein these genes, and also have found that these mutant microorganisms have a high ability to produce propanol, compared to existing mutant microorganisms, thereby completing the present invention.

SUMMARY OF THE INVENTION

It is an object of the present invention to provide a method for preparing a mutant microorganism having the ability to produce propanol in high concentration and high yield, and a mutant microorganism prepared thereby.

Another object of the present invention is to provide a method of producing propanol using said mutant microorganism.

To achieve the above objects, the present invention provides a method for preparing a mutant microorganism having the ability to produce propanol in high concentration and high yield, the method comprising:

(a) introducing or amplifying a threonine dehydratase-encoding gene in a microorganism having threonine-producing ability;

(b) introducing or amplifying a gene, which encodes an enzyme that converts 2-ketobutyrate to propionate, a gene, which encodes an enzyme that converts propionate to propinyl-CoA, and a gene, which encodes an enzyme that converts propinyl-CoA to propanol, in the microorganism;

(c) introducing or amplifying a gene, which encodes an enzyme that converts acetyl-CoA and pyruvate to 2-ketobutyrate, in the microorganism; and (d) disrupting or inactivating genes, which encode acetolactate synthase III and acetolactate synthase I, in the microorganism.

The present invention also provides a mutant microorganism having the ability to produce propanol in high concentration and high yield, the mutant microorganism is characterized by:

(a) a threonine dehydratase-encoding gene is introduced or amplified;

(b) a gene, which encodes an enzyme that converts 2-ketobutyrate to propionate, a gene, which encodes an enzyme that converts propionate to propinyl-CoA, and a gene, which encodes an enzyme that converts propinyl-CoA to propanol, are introduced or amplified;

(c) a gene, which encodes an enzyme that converts acetyl-CoA and pyruvate to 2-ketobutyrate, is introduced or amplified; and (d) genes encoding acetolactate synthase III and acetolactate synthase I are disrupted or inactivated, in a microorganism having threonine-producing ability.

The present invention also provides a method of producing propanol, the method comprising: culturing said mutant microorganism.

BRIEF DESCRIPTION OF THE DRAWINGS

The above and other objects, features and advantages of the present invention will be apparent from the following detailed description of the preferred embodiments of the invention in conjunction with the accompanying drawings, in which.

DETAILED DESCRIPTION OF THE PREFERRED EMBODIMENTS

Figure 1:
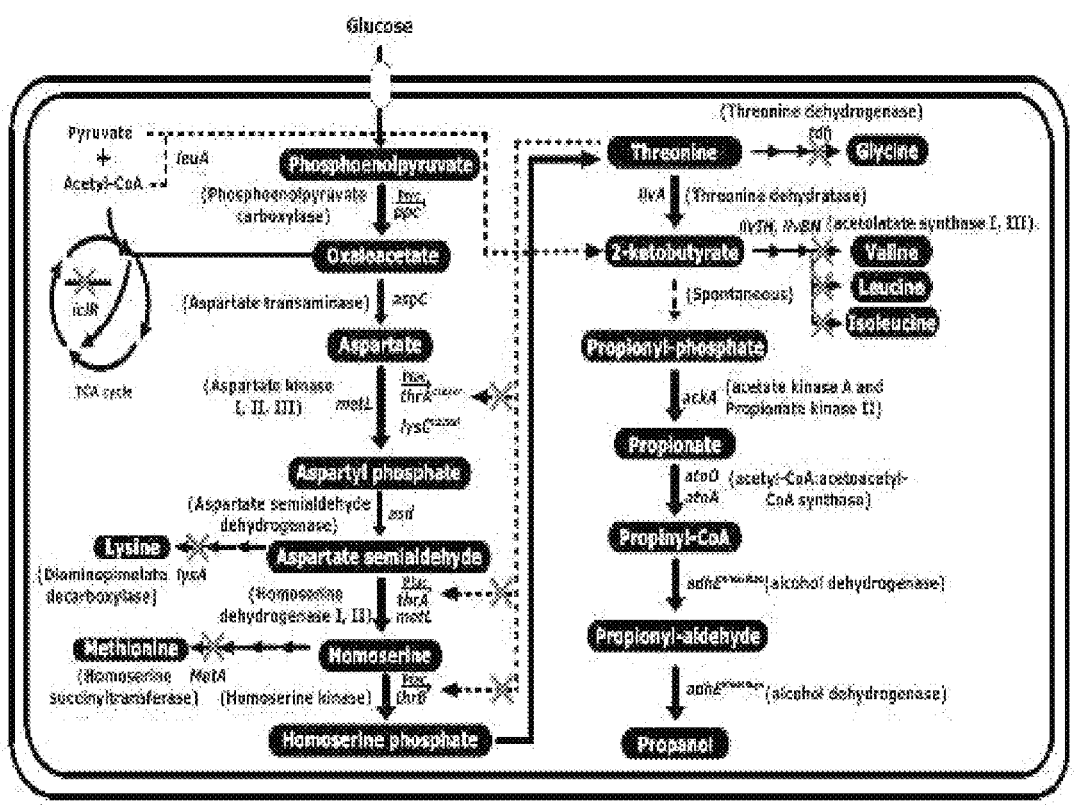
FIG. 1 shows a metabolic pathway in which propanol is biosynthesized from 2-ketobutyrate in a microorganism having threonine-producing ability.

Unless defined otherwise, all technical and scientific terms used herein have the same meaning as commonly understood by one of ordinary skill in the art to which the invention pertains. Generally, the nomenclature used herein and the experiment methods which will be described later are those well known and commonly employed in the art.

In the present invention, genes, which encode enzymes that are involved in the biosynthesis of propanol from 2-ketobutyrate, were introduced into a microorganism having threonine-producing ability so that the metabolic pathway that converts 2-ketobutyrate to propanol was newly constructed, thereby constructing a mutant microorganism having an improved ability to produce propanol. In addition, whether the constructed mutant microorganism is capable of synthesizing propanol was examined.

In one aspect, the present invention is directed to a method for preparing a mutant microorganism having the ability to produce propanol in high concentration and high yield, the method comprising:

(a) introducing or amplifying a threonine dehydratase-encoding gene in a microorganism having threonine-producing ability;

(b) introducing or amplifying a gene, which encodes an enzyme that converts 2-ketobutyrate to propionate, a gene, which encodes an enzyme that converts propionate to propinyl-CoA, and a gene, which encodes an enzyme that converts propinyl-CoA to propanol, in the microorganism;

(c) introducing or amplifying a gene, which encodes an enzyme that converts acetyl-CoA and pyruvate to 2-ketobutyrate, in the microorganism; and (d) disrupting or inactivating genes encoding acetolactate synthase III and acetolactate synthase I, in the microorganism.

The microorganism having threonine-producing ability, which is used in the present invention, may be selected from among bacteria, yeasts, fungi and the like, in which the bacteria are preferably selected from among *Corynebacterium* sp., *Brevibacterium* sp., and *E. coli*, but any bacteria having threonine-producing ability may be used without limitation in the present invention.

As used herein, the term "introducing" or "amplifying" is meant to include mutating, replacing or deleting part of the gene of interest, or introducing one or more bases into the gene, or introducing a gene from another microorganism, which encodes the same enzyme, so as to increase the activity of the corresponding enzyme.

As used herein, the term "inactivating" is meant to include mutating, replacing or deleting part of the gene of interest, or introducing one or more bases into the gene, so as to reduce the activity of an enzyme, which is expressed by the gene, thereby blocking part, or a substantial part, of the biosynthetic pathway in which the enzyme of the gene is involved.

As used herein, the term "disrupting" is meant to include mutating, replacing or deleting part or all of the gene of interest, or introducing one or more bases into the gene, such that the gene is not expressed or does not exhibit enzymatic activity, even though it is expressed, thereby blocking the biosynthetic pathway in which the gene is involved.

The gene that encodes threonine dehydratase may be *E. coli* ilvA. In addition to the *E. coli* ilvA gene, genes that encode ilvA from other microorganisms may also be used in the present invention, as long as they are expressed in host cells and show the same activity as the *E. coli* ilvA gene.

The genes that encode acetolactate synthase III may be *E. coli* ilvI and ilvH. In addition to the *E. coli* ilvI and ilvH genes, genes that encode ilvI and ilvH from other microorganisms may also be used in the present invention, as long as they are expressed in host cells and show the same activity as the *E. coli* genes.

The genes that encode acetolactate synthase I may be *E. coli* ilvB and ilvN. In addition to the *E. coli* ilvB and ilvN genes, genes that encode ilvB and ilvN from other microorganisms may also be used in the present invention, as long as they are expressed in host cells and show the same activity as the *E. coli* genes.

The enzyme that converts 2-ketobutyrate to propionate may be acetate kinase A or propionate kinase III, and the gene that encodes acetate kinase A or propionate kinase III may be *E. coli* ackA. In addition to the *E. coli* ackA gene, genes that encode ackA from other microorganisms may also be used in the present invention, as long as they are expressed in host cells and show the same activity as the *E. coli* genes.

The enzyme that converts propionate to propinyl-CoA may be acetyl-CoA:acetoacetyl-CoA synthase, and the genes that encode acetyl-CoA:acetoacetyl-CoA synthase may be *E. coli* atoD and atoA. In addition to, the *E. coli* atoD and atoA genes, genes that encode atoD and atoA from other microorganisms may also be used in the present invention, as long as they are expressed in host cells and show the same activity as the *E. coli* genes.

The enzyme that converts propinyl-CoA to propanol may be alcohol dehydrogenase, and the gene that encodes alcohol dehydrogenase may be *E. coli* adhE$^{mu}$. In addition to the *E. coli* adhE$^{mu}$ gene, genes that encode adhE$^{mu}$ from other microorganisms may also be used in the present invention, as long as they are expressed in host cells and show the same activity as the *E. coli* genes.

The enzyme that converts acetyl-CoA and pyruvate to 2-ketobutyrate may be (R)-citramalate synthase, and the gene that encodes (R)-citramalate synthase may be leuA from *Methanosarcina acetivorans*. In addition to the leuA gene from *Methanosarcina acetivorans*, genes that encode leuA from other microorganisms may also be used in the present invention, as long as they are expressed in host cells and show the same activity as the leuA gene from *Methanosarcina acetivorans*.

In another aspect, the present invention is directed to a mutant microorganism having the ability to produce propanol in high concentration and high yield, the mutant microorganism is characterized by:

(a) a threonine dehydratase-encoding gene is introduced or amplified;

(b) a gene, which encodes an enzyme that converts 2-ketobutyrate to propionate, a gene, which encodes an enzyme that converts propionate to propinyl-CoA, and a gene, which encodes an enzyme that converts propinyl-CoA to propanol, are introduced or amplified;

(c) a gene, which encodes an enzyme that converts acetyl-CoA and pyruvate to 2-ketobutyrate, is introduced or amplified; and (d) genes encoding acetolactate synthase III and acetolactate synthase I are disrupted or inactivated, in a microorganism having threonine-producing ability.

In still another aspect, the present invention is directed to a method of producing propanol by culturing said mutant microorganism.

Hereinafter, the present invention will be described in further detail with reference to examples. It will be obvious to a person having ordinary skill in the art that these examples are illustrative purposes only and are not to be construed to limit the scope of the present invention.

Although E. coli W3110 was particularly used as a host microorganism in the following examples, it will be obvious to those skilled in the art that genes coding for enzymes which are involved in the biosynthesis of propanol from 2-ketobutyrate may also be introduced into other E. coli strains, bacteria, yeasts or fungi, which are then used to produce propanol.

Moreover, although the following examples illustrated introducing genes from specific strains, it will be obvious to those skilled in the art that other genes may also be introduced, as long as they are expressed in host cells and show the same activity as the genes used in the examples.

In addition, although the following examples illustrated only specific media and culture methods, it will be obvious to those skilled in the art either to use hydrolysates such as whey or CSL (corn steep liquor) as reported in the literature or to use various culture methods such as fed-batch culture or continuous culture (Lee et al., Bioprocess Biosyst. Eng., 26: 63, 2003; Lee et al., Appl. Microbiol. Biotechnol., 58: 663, 2002; Lee et al., Biotechnol. Lett., 25: 111, 2003; Lee et al., Appl. Microbiol. Biotechnol., 54: 23, 2000; Lee et al., Biotechnol. Bioeng., 72: 41, 2001).

EXAMPLE 1

Construction of Microbial Strain Having High Ability to Produce L-threonine 1-1: Construction of pSacHR06

Figure 2:
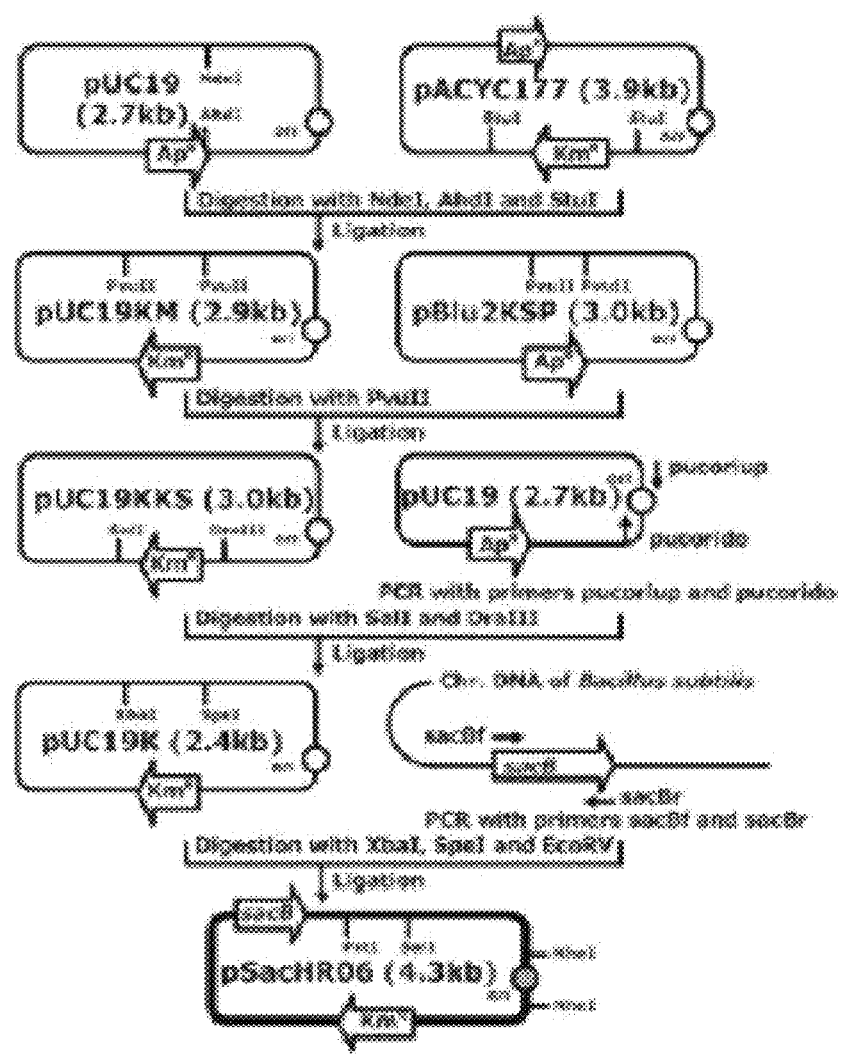
FIG. 2 shows a process for constructing a pSacHR06 vector.

In order to disrupt feedback inhibition of thrA, a pSacHR06 vector was constructed for the purpose of using homologous recombination of sacB originated from *Bacillus subtilis* (Wohlleben et. al., J. Bacteriol., 174:5462, 1992) to substitute a specific base or bases of chromosomal DNA (see FIG. 2).

First, in order to substitute the ampicillin resistance gene of a pUC19 vector (New England Biolab, USA) with kanamycin resistance, a 1.5 kb fragment obtained by digesting the pUC19 vector with NdeI and AhdI was ligated with a 1.3 kb fragment obtained by digesting a pACYC177 vector (New England Biolabs, USA) with StuI, thus obtaining a pUC19KM vector.

Then, a 2.5 kb fragment obtained by digesting the pUC19KM vector with PvuII was ligated with a 400 bp fragment obtained by digesting a pBluescriptIIKS(+) vector with PvuII, thus obtaining a pUC19KKS vector. In order to make it possible to easily remove a DNA replication origin from the pUC19KKS vector, the pUC19 vector as a template was subjected to PCR using primers of SEQ ID NOs: 1 and 2, thus obtaining a DNA fragment, having a DNA replication origin and the same restriction enzyme recognition sites at both terminal ends thereof, respectively. The fragment was digested with SalI and DraIII and ligated with a 1.5 kb fragment obtained by digesting a pUC19KKS vector with SalI and DraIII, thus obtaining a pUC19K vector. In order to introduce a *Bacillus subtilis* sacB gene into the pUC19K vector, the genomic DNA template of *Bacillus subtilis* was subjected to PCR using primers of SEQ ID NOs: 3 and 4, thus synthesizing a DNA fragment containing a sacB gene, and the synthesized DNA fragment and the pUC19K vector were digested with XbaI and SpeI and were ligated with each other, thus constructing a pSacHR06 vector having a sacB gene (see FIG. 2).

The pSacHR06 vector can be used in sacB positive selection, because it has the *Bacillus subtilis*-derived sacB gene, and the removal of the DNA replication origin and the re-ligation of the vector can be easily achieved using restriction enzymes.

```
pucoriup:
                                        (SEQ ID NO: 1)
5'-agccgtcgacgctagcgcatgcacgcgtgtgcacccatgggacgtcc tcactgactcgctgcgctc-3' pucorido:
                                        (SEQ ID NO: 2)
5'-ggctcacaacgtggctagcgacgtcgtgcacccatgggttccactga gcgtcagacc-3 sacBf:
                                        (SEQ ID NO: 3)
5'-actctctagacgcgggtttgttactgataa-3' sacBr:
                                        (SEQ ID NO: 4)
5'-gctagatatcaggatatcggcattttctttt-3'
```

1-2: Deletion of lacI Gene from E. coli W3110

In L-valine-producing microorganism E. coli W3110 (ATTC 39936), deletion of lacI gene, which encodes a lac operon repressor and functions to inhibit the transcription of a lac operon that performs lactose degradation, and removal of antibiotic resistance, were performed using primers of SEQ ID NOs: 5 and 6 by a one-step inactivation method (Warner et al., PNAS, 97(12):6640-6645, 2000).

```
lacI_1stup:
                                        (SEQ ID NO: 5)
5'-gtgaaaccagtaacgttatacgatgtcgcagagtatgccggtgtctc ttagattgcagcattacacgtcttg-3' lacI_1stdo:
                                        (SEQ ID NO: 6)
5'-tcactgcccgctttccagtcgggaaacctgtcgtgccagctgcatta atgcacttaacggctgacatggg-3'
```

1-3: Removal of Feedback Inhibition of thrA

Using the homologous recombination vector pSacHR06 constructed in Example 1-1 and the W3110ΔlacI constructed in Example 1-2 and with reference to Lee et al., J. Bacteriol., 185:5442, 2003, feedback inhibition of thrA that encodes aspartokinase I was eliminated.

Specifically, the chromosomal DNA of E. coli W3110 (ATTC 39936) was isolated and purified according to the known method (Sambrook et al., *Molecular Cloning*, 2nd ed., Cold Spring Harbor Laboratory Press, NY, 1989). Then, PCR was performed using the chromosomal DNA as a template with primers of SEQ ID NOs: 7 and 8 and primers of SEQ ID NOs: 9 and 10, and the obtained two PCR fragments were mixed with each other at the same concentration. Then, the mixture was subjected to overlapping PCR using primers of SEQ ID NOs: 7 and 10. The obtained 1279-bp PCR fragment was digested with BamHI and SalI enzymes and inserted into the homologous recombination vector pSacHR06 digested with BamHI and SalI enzymes. Then, the PCR fragment was sequenced, and as a result, it was confirmed that the 1034$^{th}$ base (C) of thrA was substituted with T.

The obtained vector was digested with a NheI enzyme to remove the replication origin, after which it was self-ligated and then electroporated into the electroporation-competent cells of W3110ΔlacI. Then, a strain, from which feedback inhibition of thrA has been eliminated, was collected by sacB positive selection.

thrA1:
(SEQ ID NO: 7)
5'-acgcggatccatcgccattatggccggcgtattagaagc-3' thrA2:
(SEQ ID NO: 8)
5'-gattgcgtaatcagcaccacgaaaatacgggcgcgtgacatcg-3' thrA3:
(SEQ ID NO: 9)
5'-cgatgtcacgcgcccgtattttcgtggtgctgattacgcaatc-3' thrA4:
(SEQ ID NO: 10)
5'-cacgcgtcgacctggaagtgcagttaacaatgaccggg-3'

1-4: Removal of Feedback Inhibition of lysC

With reference to the reported research results (Ogawa-Myyata et al., Biosci. Biotechnol. Biochem., 65:1149, 2001), feedback inhibition of the lysC gene coding for aspartokinase III was eliminated from the strain from which feedback inhibition of thrA has been eliminated as described in Example 1-3. Specifically, PCR was performed using the chromosomal DNA of *E. coli* W3110 (ATTC 39936) as a template and a primer pair of SEQ ID NOs: 11 and 12 and a primer pair of SEQ ID NOs: 13 and 14, and the obtained two PCR fragments were mixed with each other at the same concentration. Then, the mixture was subjected to overlapping PCR using a primer pair of SEQ ID NOs: 11 and 14. The obtained 1484-bp PCR fragment was digested with BamHI and SalI enzymes and inserted into the homologous recombination vector pSacHR06 digested with BamHI and SalI enzymes. Then, the PCR fragment was sequenced, and as a result, it was confirmed that the 1055$^{th}$ base (C) of lysC was substituted with T.

The obtained vector was digested with a NheI enzyme to remove the replication origin, after which it was self-ligated and then electroporated into the electroporation-competent cells of the *E. coli* strain (constructed in Example 1-3) from feedback inhibition of thrA has been eliminated. Then, a strain, from which feedback inhibition of lysC has been eliminated, was collected by sacB positive selection.

lysC1:
(SEQ ID NO: 11)
5'-ctgatgtcgaccctgctgtttgttgagatcctgcgc-3' lysC2:
(SEQ ID NO: 12)
5'-ggttgaaccggtggtatcaaggataatgccacgctcacttctg-3' lysC3:
(SEQ ID NO: 13)
5'-cagaagtgagcgtggcattaatccttgataccaccggttcaacc-3' lysC4:
(SEQ ID NO: 14)
5'-ccagctaaatgacgcttcaggatccggtttataag-3'

1-5: Substitution of Threonine Operon thrABC with Promoter

In order to disrupt regulation of transcriptional expression by attenuation in the *E. coli* strain W3110 (constructed in Example 1-4) from which feedback inhibition of the thrA gene and feedback inhibition of the lysC gene were eliminated, a threonine operon promoter comprising an attenuator sequence was substituted with a strong tac promoter.

For this purpose, PCR was performed using the genomic DNA of *E. coli* W3110 as a template and a primer pair of SEQ ID NOs: 15 and 16, thus obtaining a 725 bp PCR fragment. The obtained PCR fragment was digested with PvuII and SphI and cloned into the corresponding enzyme digestion sites of a pKK223-3 vector (Pharmacia Biotech, USA).

Meanwhile, PCR was performed using primers of SEQ ID NOs: 17 and 18, thus obtaining a 705-bp fragment. The obtained fragment was digested with EcoRI and PstI and ligated and cloned into a pKK223-3 vector digested with the same enzymes. The vector was sequenced, and then digested with PvuII and PstI and ligated with the pSacHR06 vector digested with the same enzymes. Then, the resulting vector was transformed into the *E. coli* strain W3110 from which feedback inhibition of the thrA gene and feedback inhibition of the lysC gene have been eliminated, thereby constructing an *E. coli* strain in which the promoter containing an attenuator was substituted with tac promoter.

thrAT1:
(SEQ ID NO: 15)
5'-gcagccagctgtagcgatctgcggattgtcgatagt-3' thrAT2:
(SEQ ID NO: 16)
5'-caggagcatgccagaagctgctatcagacactcttt-3' thrAT3:
(SEQ ID NO: 17)
5'-cagcagaattcatgcgagtgttgaagttcggcggta-3' thrAT4:
(SEQ ID NO: 18)
5'-cagagctgcagtccgtccaaatctcgcaacaatcgg-3'

1-6: Disruption of lysA, metA, tdh and iclR Genes

In the W3110 strain (constructed in Example 1-5) from which the lacI gene and feedback inhibition of the thrA gene and feedback inhibition of the lysC gene were been eliminated and in which the promoter of the thrABC operon was substituted with tac promoter, lysA, metA, tdh and iclR genes were disrupted by one-step inactivation (Warner et al., PNAS, 6:6640, 2000), and an antibiotic resistance marker gene was removed.

Specifically, in order to construct a strain deficient in lysA gene coding for diaminopimelate decarboxylase, a PCR reaction was performed using a primer pair of SEQ ID NOs: 19 and 20 and a pKD4 plasmid (Warner et al., PNAS, 6; 6640, 2000), and the resulting DNA fragment was cloned into pKD46 (Warner et al., PNAS, 6; 97(12):6640, 2000, GenBank No. AY048746), and then electroporated into the electroporation-competent cells of W3110 obtained in Example 1-4.

Then, a PCR reaction was performed on a kanamycin-resistant cell line to confirm the disruption of the lysA gene, and a pCP20 plasmid (Warner et al., PNAS, 6:6640, 2000) was introduced into the cell line to remove an antibiotic resistance marker gene.

KOlysA1:
(SEQ ID NO: 19)
5'-atgccacattcactgttcagcaccgataccgatctcaccgccgaaaa
tctgattgcagcattacacgtcttg-3'

KOlysA2:
(SEQ ID NO: 20)
5'-gttgataaggaacagaaagcccaccgcccgcagaaatagcctgtaaa
tcccacttaacggctgacatggga-3'

In order to construct a strain deficient in metA gene coding for homoserine O-succinyltransferase, the metA gene was disrupted by one-step inactivation using primers of SEQ ID NOs: 21 and 22, and an antibiotic resistance marker gene was removed.

KOmetA1:
(SEQ ID NO: 21)
5'-gtgtgccggacgagctacccgccgtcaatttcttgcgtgaagaaaac gtctttgtgattgcagcattacacgtcttg-3'

KOmetA2:
(SEQ ID NO: 22)
5'-cgggatggcccgtcacaaaggcaatgcgcttatctttactggcaaac agacacttaacggctgacatggga-3'

In order to construct a strain deficient in tdh gene coding for L-threonine dehydrogenase, the tdh gene was disrupted by one-step inactivation using primers of SEQ ID NOs: 23 and 24, and an antibiotic resistance marker gene was removed.

KOtdh1:
(SEQ ID NO: 23)
5'-atgaaagcgttatccaaactgaaagcggaagagggcatctggatgac cgagattgcagcattacacgtcttg-3'

KOtdh2:
(SEQ ID NO: 24)
5'-atcactttggtccagtcgatagacatatcagacggcggaatacccag catcacttaacggctgacatggga-3'

In order to construct a strain deficient in iclR gene coding for a regulatory protein that inhibits the expression of glyoxylate shunt, the iclR gene was disrupted by one-step inactivation using primers of SEQ ID NOs: 25 and 26, and an antibiotic resistance marker gene was removed.

KOiclR1:
(SEQ ID NO: 25)
5'-tgaaaatgatttccacgatacagaaaaaagagactgtcatggtcgca cccgattgcagcattacacgtcttg-3'

KOiclR2:
(SEQ ID NO: 26)
5'-atagaaattgcggcaaacggttcacggtgctcatcgaaaatacacgc tgccacttaacggctgacatggga-3'

1-7: Construction of Strain Having Decreased Threonine Dehydratase Activity

In order to increase the production of L-threonine by reducing the amount of L-isoleucine produced using L-threonine as a substrate, a strain was constructed by generating a site specific mutation in the ilvA gene coding for threonine dehydratase which is the first enzyme of the corresponding pathway, with reference to the research results of Lee et al. (Lee et al., *J. Bacteriol.*, 185:5442, 2003), and it was confirmed that the growth of the constructed strain was significantly influenced by the concentration of L-isoleucine in a medium.

Specifically, the ilvA gene was disrupted by one-step inactivation using the chromosomal DNA of *E. coli* W3110 (ATCC 39936) as a template with primers of SEQ ID NO: 27 and SEQ ID NO: 28, and a chloramphenicol-resistant cell line was selected. The disruption of the ilvA gene in the selected cell line was confirmed by PCR.

Meanwhile, PCR was performed using the chromosomal DNA of *E. coli* W3110 (ATCC 39936) as a template with primers of SEQ ID NOs: 29 and 30 and primers of SEQ ID NOs: 31 and 32, thus obtaining a 648-bp fragment and a 676-bp fragment. The obtained two PCR fragments were mixed with each other at the same concentration. Then, the mixture was subjected to overlapping PCR using primers of SEQ ID NOs: 29 and 32. The resulting 1287-bp PCR fragment was digested with BamHI and SalI enzymes and inserted into the vector pSacHR06 digested with BamHI and SalI enzymes. Then, the PCR fragment was sequenced, and as a result, it was confirmed that the 290$^{th}$ base (C) of ilvA was substituted with T. The obtained vector was digested with a NheI enzyme to remove the replication origin, after which it was self-ligated and then electroporated into the electroporation-competent cells of the mutant strain constructed in Example 1-6. Then, a strain having a decreased weak threonine dehydratase activity was collected by sacB positive selection (Wohlleben et al., *J. Bacteriol.*, 174:5462, 1992) and a chloramphenicol-sensitive selection.

KOilvA1:
(SEQ ID NO: 27)
5'-atcgccagccagtgcacagctttaagctgcgcggcgcatacgccatg atggattgcagcattacacgtcttg-3'

KOilvA2:
(SEQ ID NO: 28)
5'-cccctgctgctgtgacagttcgatcgctttggctttcgcttcatcaa agtcacttaacggctgacatggga-3' ilvA1:
(SEQ ID NO: 29)
5'-gacgggatccgcaaagcctgtgcgctgatcaccgacgg-3' ilvA2:
(SEQ ID NO: 30)
5'-cacgcctaaccgcgcagaaaaaaacgcgacgccctgcg-3' ilvA3:
(SEQ ID NO: 31)
5'-cgcagggcgtcgcgttttttctgcgcggttaggcgtg-3' ilvA4:
(SEQ ID NO: 32)
5'-caggtactgcagaccggaaagaatatgcgccagccgttcg-3'

1-8: Construction of Plasmid pMloxC

If genes are disrupted by one-step inactivation, one FRT or loxP sequence, which is a recombinase recognition site, will remain in the chromosomal DNA after disruption of each gene. For this reason, it is difficult to construct mutant strains, because non-targeted sites are disrupted when continuous disruption of large amounts of genes is performed (Nagy A., *Genesis*, 26:99, 2000). Suzuki et al. proposed an improved method for disrupting genes using mutant loxP, named lox71 and lox66, in order to solve this problem (*Appl. Environ. Microbiol.*, 71:8472, 2005). Accordingly, the present inventors constructed the new vector pMloxC into which lox71 and lox66 were introduced (*Nucleic Acids Res.*, 24:2519, 1996), in order to more easily use this method.

Figure 3:
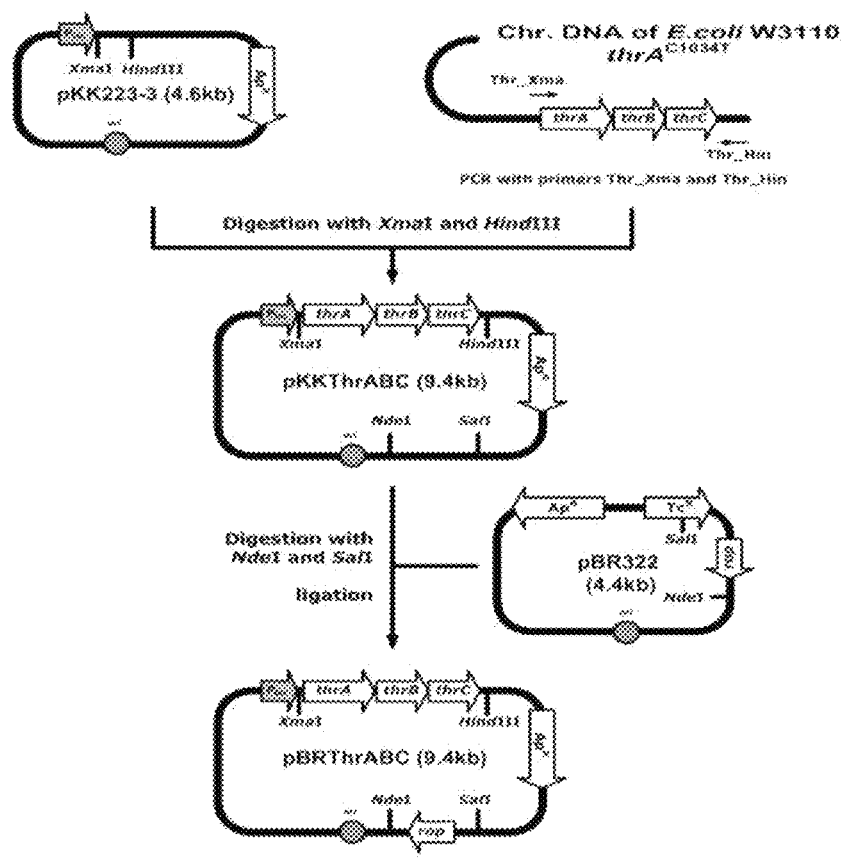
FIG. 3 shows a process for constructing the recombinant vector pBRThrABC comprising a thrABC operon.

Specifically, a pUG6 plasmid (Nucleic Acids Res., 24:2519, 1996) was digested with HindIII and EcoRV to obtain a 2,427-bp DNA fragment, and PCR was performed a pACYC184 plasmid (New England Biolab., USA) as a template with primers of SEQ ID NO:33 and SEQ ID NO:34, thus obtaining a 1,100-bp PCR fragment. The obtained fragments were digested with EcoRV/HindIII and HindIII/SmaI, respectively, and then ligated with each other, thereby constructing pMloxC (see FIG. 3).

ECmulox_up:
(SEQ ID NO: 33)
5'-atataagctttaccgttcgtatagcatacattatacgaagttatctg ccctgaaccgacgaccg-3'

ECmulox_do:
(SEQ ID NO: 34)
5'-aattcccgggtaccgttcgtataatgtatgctatacgaagttatgca tcacccgacgcactttgc-3'

1-9: Disruption of tdcC Gene

In order to construct a strain deficient in tdcC gene coding for threonine/serine transporter, PCR was performed using the pMloxC vector (constructed in Example 1-8) as a template with primers of SEQ ID NOs: 35 and 36, and the resulting DNA fragment was isolated and purified. Then, PCR was performed using the purified DNA fragment as a template with primers of SEQ ID NO:37 and SEQ ID NO: 38.

Using the resulting DNA fragment, tdcC gene was disrupted by the above-described one-step inactivation method, and an antibiotic resistance marker gene was removed.

KOtdcC1:
(SEQ ID NO: 35)
5'-gcgtaaatcagataccacatggacgttaggcttgtttggtacggcaa tcgtaggtgacactatagaacgcg-3'

KOtdcC3:
(SEQ ID NO: 36)
5'-ccagtgtaatcgcgaacgttgttttggtaccggtcatggacgcaaag tggtagtggatctgatgggtacc-3'

KOtdcC2:
(SEQ ID NO: 37)
5'-atgagtacttcagatagcattgtatccagccagacaaaacaatcgtc ctggcgtaaatcagataccacat-3'

KOtdcC4:
(SEQ ID NO: 38)
5'-gaagaaagatttgaagatagccacgagtgcgatgatggaagccgcat attccagtgtaatcgcgaacgt-3'

1-10: Substitution of Promoter of ppc Gene

The promoter of the ppc gene encoding phosphoenolpyruvate carboxylase on the chromosome was substituted with a strong promoter, thus constructing a strain having increased enzyme activity. In order to substitute the promoter of the ppc gene, PCR was performed using the above-constructed pMloxC plasmid as a template and primers of SEQ ID NO: 39 and SEQ ID NO: 40, and then PCR was further performed using the resulting DNA fragment as a template with primers of SEQ ID NO: 41 and SEQ ID NO: 42. Then, PCR was further performed using the resulting DNA fragment as a template with primers of SEQ ID NO: 43 and SEQ ID NO: 44. Then, the resulting DNA fragment was inserted in the ppc gene using the same method as the above-described one-step inactivation method, and an antibiotic resistance marker gene was removed, thereby constructing a strain in which the native promoter of ppc was substituted with a stronger trc promoter.

FPppc1:
(SEQ ID NO: 39)
5'-ctgcgggcaaccatgcgcaagggtttccctctcctgcgcgatgctg ggttaggtgacactatagaacgcg-3'

RPppc1:
(SEQ ID NO: 40)
5'-tctgcgctttggcttccgccatgttggccggagacagagtaaacagg cagctaaaggcaaagaac-3'

FPppc2:
(SEQ ID NO: 41)
5'-attaagttcactgaccgatgcggaaaaacgcaaaggcgtggtggcct gttctgcgggcaaccatgcgcaa-3'

RPppc2:
(SEQ ID NO: 42)
5'-ctgcgggcaaccatgcgcaaggggtttccctctcctgcgcgatgctg ggttaggtgacactatagaacgcg-3'

FPppc3:
(SEQ ID NO: 43)
5'-ggcagctaaaggcaaagaacatcaccactgcaaccatcagcatgctt agtggatctgatgggtacc-3'

RPppc3:
(SEQ ID NO: 44)
5'-attaagttcactgaccgatgcggaaaaacgcaaaggcgtggtggcct gttctgcgggcaaccatgcgcaa-3'

1-11: Substitution of Promoter of acs Gene

In order to reduce the amount of acetic acid produced during Fed-batch culture of a threonine-producing strain, a strain having increased enzyme activity was constructed by substituting the promoter of the acetyl CoA synthetase-encoding acs gene on the chromosome with a strong promoter. To substitute the promoter of acs, PCR was performed using the above-constructed pMloxC plasmid as a template with primers of SEQ ID NO: 45 and SEQ ID NO: 46, and then PCR was further performed using the resulting DNA fragment as a template with primers of SEQ ID NO: 47 and SEQ ID NO: 48. Then, PCR was further performed using the resulting DNA fragment as a template with primers of SEQ ID NO: 49 and SEQ ID NO: 50. Then, the resulting DNA fragment was inserted in the acs gene using the same method as the above-described one-step inactivation method, and then an antibiotic resistance marker gene was removed, thereby constructing a strain in which the native promoter of acs was substituted with a stronger trc promoter.

FPacs1:
(SEQ ID NO: 45)
5'-gcccctatgtgtaacaaataaccacactgtgaatgttgtctaggtga cactatagaacgcg-3'

RPacs1:
(SEQ ID NO: 46)
5'-tgttatccgctcacaattccacacattatacgagccggatgattaat tgtcaacagctagtggatctgatgggtacc-3'

FPacs2:
(SEQ ID NO: 47)
5'-tcacgacagtaaccgcacctacactgtcatgacattgctcgcccta tgtgtaacaaata-3'

RPacs2:
(SEQ ID NO: 48)
5'-cgatgttggcaggaatggtgtgtttgtgaatttggctcatggtctgt ttcctgtgtgaaattgttatccgctcacaattcc-3'

```
-continued
FPacs3:
                                           (SEQ ID NO: 49)
5'-cgaattgcgccattgttgcaatggcggttttattgttttcacgac
agtaaccgcacct-3'

RPacs3:
                                           (SEQ ID NO: 50)
5'-ttgttgatacatcgcctcgtactgctgagggtttatcaggcaacggt
ctgcgatgttggcaggaatggtg-3'
```

EXAMPLE 2

Construction of Strain Deficient in ilvIH Gene

From the strain constructed in Example 1, the ilvIH operon was disrupted by one-step inactivation (Warner et al., PNAS, 6:6640, 2000) using primers of SEQ ID NO: 51 and SEQ ID NO: 52.

```
ilvIHk/o F:
                                           (SEQ ID NO: 51)
5'-atggagatgttgtctggagccgagatggtcgtccgatcgcttatcga
tcaTAGGTGACACTATAGAACGCG-3' ilvIHk/o R::
                                           (SEQ ID NO: 52)
5'-tcaacgcattattttatcgccgcgcgaaagtccgaccacaccagagc
gagTAGTGGATCTGATGGGTACC-3'
```

EXAMPLE 3

Construction of Strain Deficient in ilvBN Gene

From the strain constructed in Example 2, the ilvBN operon was disrupted by one-step inactivation (Warner et al., PNAS, 6:6640, 2000) using primers of SEQ ID NO: 53 and SEQ ID NO: 54.

```
ilvBNk/o F:
                                           (SEQ ID NO: 53)
5'-atggcaagttcgggcacaacatcgacgcgtaagcgctttaccggcgc
agaTAGGTGACACTATAGAACGCG-3' ilvBNk/o R::
                                           (SEQ ID NO: 54)
5'-tttactgaaaaaacaccgcgatcttgttaaacatcgtcggatcggac
tgatTAGTGGATCTGATGGGTACC-3'
```

EXAMPLE 4

Restoration of Activity of ilvA Gene

In order to restore the decrease activity of threonine dehydratase to the original state, the threonine dehydratase in the *E. coli* strain constructed in Example 3 was restored to the native threonine dehydratase using the method described in Example 1-1 with primers for ilvA1, ilvA2, ilvA3 and ilv4. Specifically, PCR was performed using W3110 gDNA as a template with primers of SEQ ID NO: 55 and SEQ ID NO: 56. Also, PCR was performed using W3110 gDNA as a template with primers of SEQ ID NO: 57 and SEQ ID NO: 58. Then, the two PCR products were mixed with each other and subjected to overlapping PCR using primers of SEQ ID NO: 55 and 58, thereby obtaining native threonine dehydratase. The gene fragment obtained as described above was substituted with the native threonine dehydratase using the method described in Example 1-1.

```
ilvA1f:
                                           (SEQ ID NO: 55)
5'-atacggatcctggtgacctgatcgctatcg-3' ilvA2r:
                                           (SEQ ID NO: 56)
5'-tgttggcgaagcgcagaaacgcgcccggtgattccgggaattcgaag
ctgtaga-3' ilvA3r:
                                           (SEQ ID NO: 57)
5'-tctacagcttcgaattcccggaatcaccgggcgcgtttctgcgcttc
gccaaca-3' ilvA4r:
                                           (SEQ ID NO: 58)
5'-agtcctgcaggtggtttcgacgcaataaaa-3'
```

In order to increase the expression level of the ilvA gene, the native promoter was substituted with trc using the one-step inactivation method.

```
ilvApchF:
                                           (SEQ ID NO: 59)
5'-ccgaaccgtggcattcagttacaggtaagcgatgccgaactggcggc
gcgcgaatatttgattgcagcattacacgtcttg-3' ilvApchR:
                                           (SEQ ID NO: 60)
5'-cttaaatattcggcaccttccggagcaccggacaggggttgcgagtc
agccgtcgtggccacttaacggctgacatggg-3'
```

EXAMPLE 5

Construction of pTac15k_atoDA_tac_adhE$^{mut}$

Figure 4:
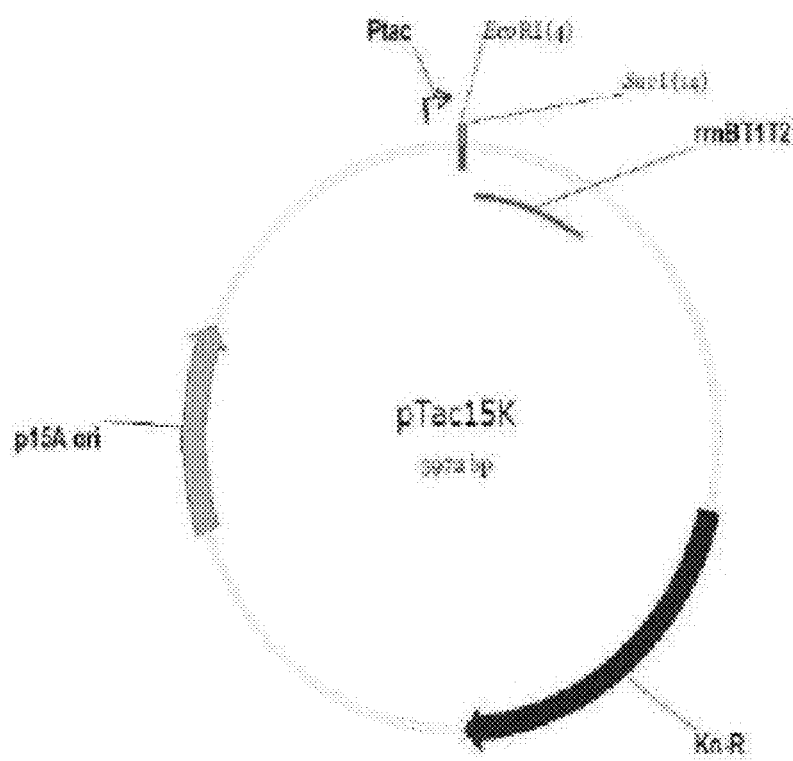
FIG. 4 shows a cleavage map of a pTac15K vector.

The trc promoter and transcription terminator of pKK223-3 (Pharmacia Biotech., Uppsala, Sweden) were inserted into pACYC177 (NEB, Beverly, Mass., USA) to construct pTac15K. The pTac15K is a constitutive expression vector having a structure shown in the cleavage map of FIG. 4. PCR was performed using the chromosomal DNA of *Escherichia coli* as a template with primers of SEQ ID NO: 61 and SEQ ID NO: 62. The resulting atoDA fragment was digested with restriction enzymes (XbaI and SphI) and ligated into the pTac15k (p15A origin, low copies, KmR; KAISTMBEL stock, tac promoter, 4.0-kb, lap stock) (Zhi-Gang Qian et al., Biotechnology and Bioengineering, 104: 651-654, 2009 and Hiszczyn' ska-Sawicka and Kur, 1997) plasmid by T4 DNA ligase, thereby constructing pTac15k_atoDA.

Figure 5:
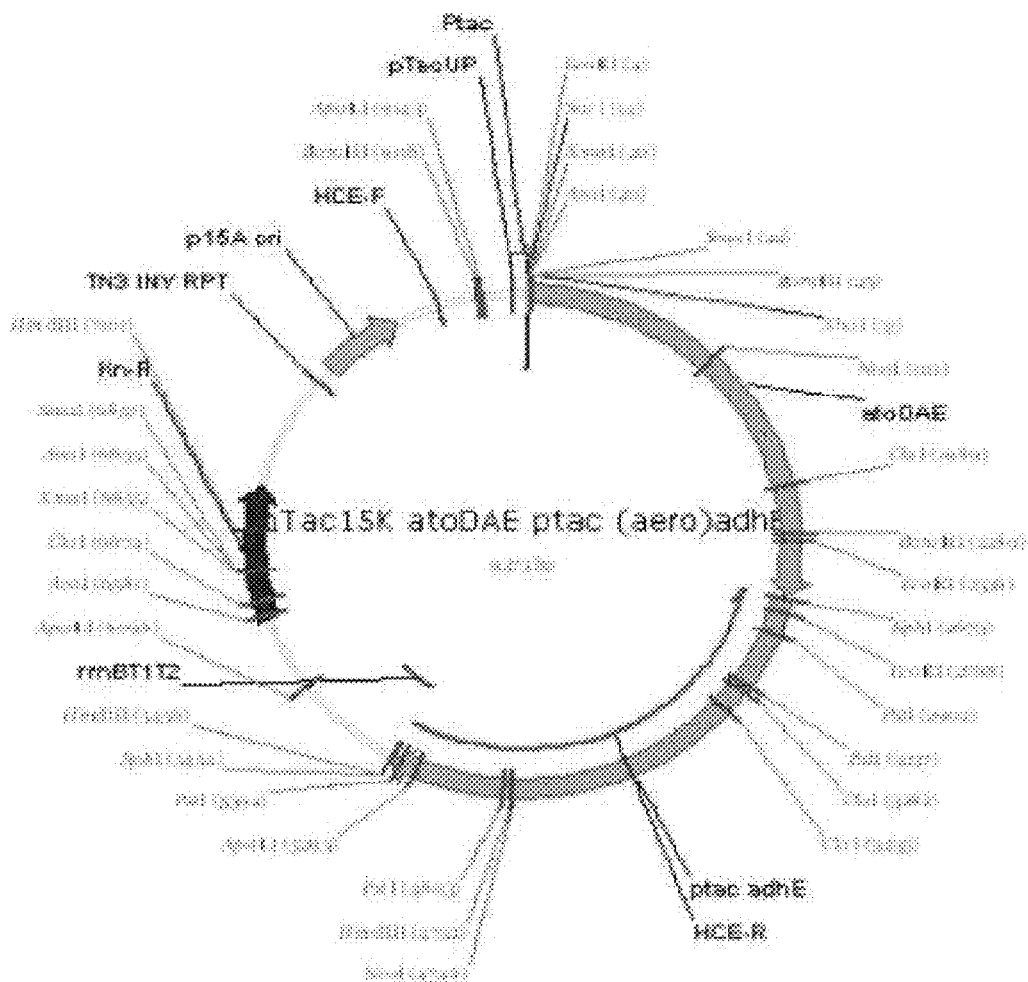
FIG. 5 shows a cleavage map of a pTac15k_atoDA_tac_adhEmut vector.

Then, PCR was performed using the chromosomal DNA of *Escherichia coli* as a template with primers of SEQ ID NO: 63 and SEQ ID NO: 64, thereby obtaining DNA fragment 1. Also, PCR was performed using the chromosomal DNA of *Escherichia coli* as a template with primers of SEQ ID NO: 65 and SEQ ID NO: 66, thereby obtaining DNA fragment 2. Then, PCR was further performed using DNA fragments 1 and 2 as a template with primers of SEQ ID NO: 62 and SEQ ID NO: 66, thereby obtaining adhE$^{mut}$. Then, PCR was further performed using the adhE$^{mut}$ DNA fragment as a template with primers of SEQ ID NOs: 66 and 67. Then, the resulting adhE$^{mut}$ fragment was digested with restriction enzymes (EcoRI and SacI) and ligated into the pTac15k_atoDA plasmid by T4 DNA ligase, thereby constructing pTac15k_atoDA_ptac_adhE$^{mut}$ (see FIG. 5). The nucleotide sequences of the primer pairs used in this Example are as follow. The adhE$^{mut}$ fragment was prepared with reference to Journal of Bacteriology, November, 2000, p. 6049-6054.

```
atoDAf:
                                         (SEQ ID NO: 61)
5'-GCCATCTAGAATGAAAACAAAATTGATGAC-3' atoDAr:
                                         (SEQ ID NO: 62)
5'-TATTGCATGCTCAGAACAGCGTTAAACCAA-3' mutadhE1:
                                         (SEQ ID NO: 63)
5'-ACTCGAGCTCGAGACAGACACTGGGAGTAA-3' mutadhE2:
                                         (SEQ ID NO: 64)
5'-TACGTCTAGATTAACCCCCCAGTTTCGATT-3 mutadhE3:
                                         (SEQ ID NO: 65)
5'-TACGTCTAGATTAACCCCCCAGTTTCGATT-3' mutadhE4:
                                         (SEQ ID NO: 66)
5'-GTGCTCTAGAAGGCCTGATCAGCTAGCTGTTTCCTGTGTGA-3' aeroadhEf:
                                         (SEQ ID NO: 67)
5'-TATAGAATTCATGGCTGTTACTAATGTCGC-3' aeroadhEr:
                                         (SEQ ID NO: 68)
5'-TATTGAGCTCTTAAGCGGATTTTTTCGCTT-3'
```

EXAMPLE 6

Construction of pBRThrABC_ptac_leuA_ptac_ackA Vector 6-1: Construction of pKKThrABC Vector In order to construct a vector containing an operon (thrABC) involved in L-threonine biosynthesis, which is the most important gene in L-threonine biosynthesis, PCR was performed using the chromosomal DNA of the mutant strain (constructed in Example 1-3), from which feedback inhibition of thrA has been released, as a template together with primers of SEQ ID NO: 21 and SEQ ID NO: 22. The resulting DNA fragment was digested with XmaI and HindIII and cloned into a pKK223-3 vector (Pharmacia Biotech, USA) digested with the same restriction enzymes, and its sequence was analyzed. As a result, a pKKThrABC containing a 9.4-kb operon (thrABC) involved in L-threonine biosynthesis was constructed.

```
Thr_Xma:
                                         (SEQ ID NO: 69)
5'-gttgcccgggatgcgagtgttgaagttcgg-3'

Thr_Hin:
                                         (SEQ ID NO: 70)
5'-gcgtcaagcttcggcggttgttattctccgc-3'
```

6-2: Construction of pBRThrABC_ptac_leuA_ptac_ackA Vector

Figure 6:
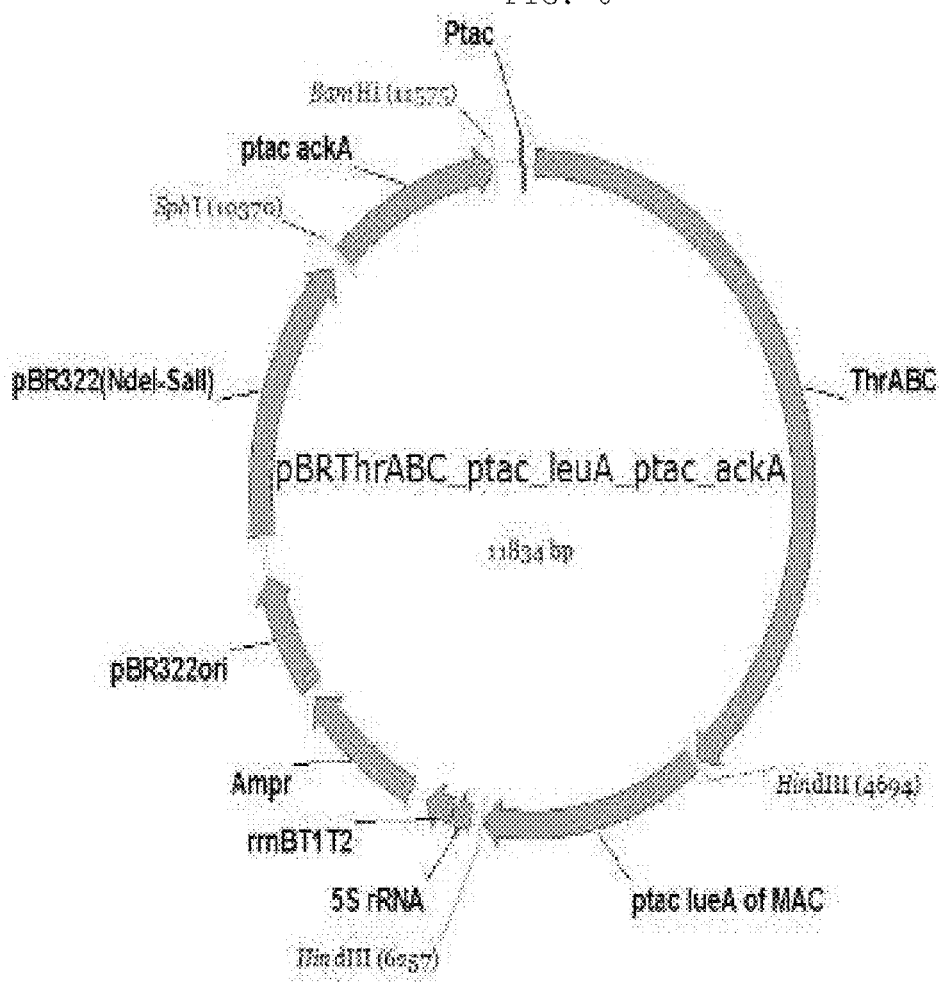
FIG. 6 shows a cleavage map of a pBRthrABC_ptac_leuA-ptac-ackA vector.

In order to increase the stability of the above-constructed pKKThrABC vector, a pBR322 vector (New England Biolab, USA) was digested with NdeI and SalI to obtain a 1.6-kb DNA fragment containing rop gene, and the pKKThrABC vector constructed in Example 6-1 was digested with the same restriction enzymes to obtain a 7.8-kb DNA fragment. The two DNA fragments were ligated with each other, thereby constructing a 9.4-kb pBRThrABC vector. In order to construct a pBRThrABC_ptac_leuA vector, PCR was performed using the genomic DNA of Methanosarcina acetivorans as a template with primers of SEQ ID NO: 71 and SEQ ID NO: 72. The resulting DNA fragment and the pBRThrABC vector were digested with the restriction enzyme HindIII and ligated with each other by T4 DNA ligase, thereby constructing a pRBThrABC_ptac_leuA vector. In addition, in order to construct a pRBThrABC_ptac_leuA_ptac_ackA vector, PCR was performed using primers of SEQ ID NO: 73 and SEQ ID NO: 74. The resulting DNA fragment and the pRBThrABC_ptac_leuA vector were digested with SphI and BamHI and ligated with each other by T4 DNA ligase, thereby constructing a pRBThrABC_ptac_leuA_ptac_ackA vector (see FIG. 6).

The primer sequences used in this Example are as follows:

```
tac_leuAf:
                                         (SEQ ID NO: 71)
5'-TATCAAGCTTTGGCAAATATTCTGAAATGA-3' tac_leuAr:
                                         (SEQ ID NO: 72)
5'-TATTAAGCTTTTACTCTTCCCGGATAAGGC-3' tac_ackAf:
                                         (SEQ ID NO: 73)
5'-TGTTGCATGCTGTGGTATGGCTGTGCAGGT-3' tac_ackAr:
                                         (SEQ ID NO: 74)
5'-TATTGGATCCTCAGGCAGTCAGGCGGCTCG-3'
```

EXAMPLE 7

Construction of Propanol-Producing Strain (PRO)

Propanol-producing microorganisms were constructed by introducing the vector, constructed in Examples 5 and 6, into the E. coli strain (constructed through the processes of Examples 1 to 4) from which feedback inhibitions of thrA and lysC have been eliminated and in which the promoter of the threonine operon has been substituted with tac promoter and the lacI, metA, lysA and tdh genes had been disrupted.

EXAMPLE 8

Measurement of the Ability to Produce Propanol

The propanol-producing microorganisms constructed in Example 7 were selected on an LB plate medium containing 50 μg/ml ampicillin and 30 μg/ml chloramphenicol. Specifically, each of the transformed mutant strain and a wild-type strain was seeded onto 10 ml of LB medium and precultured at 37° C. for 12 hours. Meanwhile, glucose (10 g/L) was added to a 250 ml flask containing 100 ml LB (sterilized at 80° C. or higher), and 1 ml of each of the precultured broths was inoculated into the flask and cultured at 31° C. for 12 hours.

As a result, as can be seen in Table 2 below, no propanol was produced in the wild-type E. coli W3110, whereas propanol was produced in the mutant strain.

TABLE 1

| Strain | Propanol (mg/L) |
|---|---|
| W3110 | ND[1] |
| PRO + pBRthrABC_tac_leuA_tac_ackA + pTac15k_atoD_atoA_tac_adhE$^{mut}$ | 6300 |

*ND: No Detection

As described above, according to the present invention, when enzymes involved in the biosynthesis of propanol are introduced into a microorganism having threonine-producing ability, the capability of the microorganism to convert threonine to propanol is increased. Thus, the present invention is useful for increasing propanol productivity which is the limitation of conventional mutant microorganisms for producing propanol.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

What is claimed is:

1. A method for preparing a mutant *E. coli* having the ability to produce propanol in high concentration and high yield, the method comprising:

(a) introducing or amplifying an ilvA gene in an *E. coli* having threonine-producing ability, wherein the ilvA gene is a threonine dehydratase-encoding gene;

(b) introducing or amplifying an ackA gene, which encodes acetate kinase A or propionate kinase III that converts 2-ketobutyrate to propionate, atoD and atoA genes, which encodes acetyl-CoA:acetoacetyl-CoA synthase that converts propionate to propinyl-CoA, and an adhE third gene, which encodes an alcohol dehydrogenase that converts propinyl-CoA to propanol, in the *E. coli*;

(c) introducing or amplifying an leuA gene, which encodes (R)-citramalate synthase that converts acetyl-CoA and pyruvate to 2-ketobutyrate, in the *E. coli*; and (d) disrupting or inactivating genes encoding acetolactate synthase III and acetolactate synthase I in the *E. coli*.

2. The method of claim 1, wherein the genes encoding acetolactate synthase III are ilvI and ilvH.

3. The method of claim 1, wherein the genes encoding acetolactate synthase I are ilvB and ilvN.

4. The method of claim 1, wherein the adhE gene is adhE$^{mut}$, which is mutated by steps comprising:

(a) obtaining DNA fragment 1 by PCR using the chromosomal DNA of *E. coli* as a template with primers of SEQ ID NO:63 and SEQ ID NO:64;

(b) obtaining DNA fragment 2 by PCR using the chromosomal DNA of *E. coli* as a template with primers of SEQ ID NO:65 and SEQ ID NO:66; and (c) obtaining adhE$^{mut}$ by PCR using the DNA fragments 1 and 2 as a template with primers of SEQ ID NO:63 and SEQ ID NO:66.

5. A mutant *E. coli* having the ability to produce propanol in high concentration and high yield, the mutant *E. coli* comprising:
- (a) an introduced or amplified ilvA gene which encodes threonine dehydratase;
- (b) an introduced or amplified ackA gene, which encodes acetate kinase A or propionate kinase III that converts 2-ketobutyrate to propionate, introduced or amplified atoD and atoA genes, which encode acetyl-CoA:acetoacetyl-CoA synthase that converts propionate to propinyl-CoA, and an introduced or amplified adhE gene, which encodes alcohol dehydrogenase that converts propinyl-CoA to propanol;
- (c) an introduced or amplified leuA gene, which encodes (R)-citramalate synthase that converts acetyl-CoA and pyruvate to 2-ketobutyrate; and
- (d) disrupted or inactivated genes encoding acetolactate synthase III and acetolactate synthase I, wherein said *E. coli* has threonine-producing ability.

6. The mutant *E. coli* of claim 5, wherein the genes that encode acetolactate synthase III are ilvI and ilvH.

7. The mutant *E. coli* of claim 5, wherein the genes that encode acetolactate synthase I are ilvB and ilvN.

8. The mutant *E. coli* of claim 5, wherein the adhE gene is adhE$^{mut}$.

9. A method of producing propanol, the method comprising: culturing the mutant *E. coli* of claim 5.

* * * * *

UNITED STATES PATENT AND TRADEMARK OFFICE
CERTIFICATE OF CORRECTION

PATENT NO. : 8,715,976 B2
APPLICATION NO. : 13/537988
DATED : May 6, 2014
INVENTOR(S) : Lee et al.

It is certified that error appears in the above-identified patent and that said Letters Patent is hereby corrected as shown below:

In the Claims

Claim 1, Column 39, Line 65: change "an adhE third gene, which encodes an alcohol dehydro-" to -- an adhE gene, which encodes an alcohol dehydro- --

Signed and Sealed this
Twenty-third Day of September, 2014

Michelle K. Lee
*Deputy Director of the United States Patent and Trademark Office*

SEQUENCE LISTING

<160> NUMBER OF SEQ ID NOS: 70

<210> SEQ ID NO 1
<211> LENGTH: 66
<212> TYPE: DNA
<213> ORGANISM: Artificial Sequence
<220> FEATURE:
<223> OTHER INFORMATION: Synthetic Construct

<400> SEQUENCE: 1
agccgtcgac gctagcgcat gcacgcgtgt gcacccatgg gacgtcctca ctgactcgct    60
gcgctc    66

<210> SEQ ID NO 2
<211> LENGTH: 57
<212> TYPE: DNA
<213> ORGANISM: Artificial Sequence
<220> FEATURE:
<223> OTHER INFORMATION: Synthetic Construct

<400> SEQUENCE: 2
ggctcacaac gtggctagcg acgtcgtgca cccatgggtt ccactgagcg tcagacc    57

<210> SEQ ID NO 3
<211> LENGTH: 30
<212> TYPE: DNA
<213> ORGANISM: Artificial Sequence
<220> FEATURE:
<223> OTHER INFORMATION: Synthetic Construct

<400> SEQUENCE: 3
actctctaga cgcgggtttg ttactgataa    30

<210> SEQ ID NO 4
<211> LENGTH: 30
<212> TYPE: DNA
<213> ORGANISM: Artificial Sequence
<220> FEATURE:
<223> OTHER INFORMATION: Synthetic Construct

<400> SEQUENCE: 4
gctagatatc aggatatcgg cattttcttt    30

<210> SEQ ID NO 5
<211> LENGTH: 72
<212> TYPE: DNA
<213> ORGANISM: Artificial Sequence
<220> FEATURE:
<223> OTHER INFORMATION: Synthetic Construct -continued

```
<400> SEQUENCE: 5
gtgaaaccag taacgttata cgatgtcgca gagtatgccg gtgtctctta gattgcagca    60
ttacacgtct tg                                                       72

<210> SEQ ID NO 6
<211> LENGTH: 70
<212> TYPE: DNA
<213> ORGANISM: Artificial Sequence
<220> FEATURE:
<223> OTHER INFORMATION: Synthetic Construct

<400> SEQUENCE: 6
tcactgcccg ctttccagtc gggaaacctg tcgtgccagc tgcattaatg cacttaacgg    60
ctgacatggg                                                          70

<210> SEQ ID NO 7
<211> LENGTH: 39
<212> TYPE: DNA
<213> ORGANISM: Artificial Sequence
<220> FEATURE:
<223> OTHER INFORMATION: Synthetic Construct

<400> SEQUENCE: 7
acgcggatcc atcgccatta tggccggcgt attagaagc                           39

<210> SEQ ID NO 8
<211> LENGTH: 43
<212> TYPE: DNA
<213> ORGANISM: Artificial Sequence
<220> FEATURE:
<223> OTHER INFORMATION: Synthetic Construct

<400> SEQUENCE: 8
gattgcgtaa tcagcaccac gaaaatacgg gcgcgtgaca tcg                      43

<210> SEQ ID NO 9
<211> LENGTH: 43
<212> TYPE: DNA
<213> ORGANISM: Artificial Sequence
<220> FEATURE:
<223> OTHER INFORMATION: Synthetic Construct

<400> SEQUENCE: 9
cgatgtcacg cgcccgtatt ttcgtggtgc tgattacgca atc                      43

<210> SEQ ID NO 10
<211> LENGTH: 38
<212> TYPE: DNA
<213> ORGANISM: Artificial Sequence
<220> FEATURE:
<223> OTHER INFORMATION: Synthetic Construct

<400> SEQUENCE: 10
cacgcgtcga cctggaagtg cagttaacaa tgaccggg                            38

<210> SEQ ID NO 11
<211> LENGTH: 36
<212> TYPE: DNA
<213> ORGANISM: Artificial Sequence
<220> FEATURE:
<223> OTHER INFORMATION: Synthetic Construct

<400> SEQUENCE: 11
ctgatgtcga ccctgctgtt tgttgagatc ctgcgc                              36
```

```
<210> SEQ ID NO 12
<211> LENGTH: 43
<212> TYPE: DNA
<213> ORGANISM: Artificial Sequence
<220> FEATURE:
<223> OTHER INFORMATION: Synthetic Construct

<400> SEQUENCE: 12
ggttgaaccg gtggtatcaa ggataatgcc acgctcactt ctg          43

<210> SEQ ID NO 13
<211> LENGTH: 44
<212> TYPE: DNA
<213> ORGANISM: Artificial Sequence
<220> FEATURE:
<223> OTHER INFORMATION: Synthetic Construct

<400> SEQUENCE: 13
cagaagtgag cgtggcatta atccttgata ccaccggttc aacc          44

<210> SEQ ID NO 14
<211> LENGTH: 35
<212> TYPE: DNA
<213> ORGANISM: Artificial Sequence
<220> FEATURE:
<223> OTHER INFORMATION: Synthetic Construct

<400> SEQUENCE: 14
ccagctaaat gacgcttcag gatccggttt ataag                   35

<210> SEQ ID NO 15
<211> LENGTH: 36
<212> TYPE: DNA
<213> ORGANISM: Artificial Sequence
<220> FEATURE:
<223> OTHER INFORMATION: Synthetic Construct

<400> SEQUENCE: 15
caggagcatg ccagaagctg ctatcagaca ctcttt                  36

<210> SEQ ID NO 16
<211> LENGTH: 36
<212> TYPE: DNA
<213> ORGANISM: Artificial Sequence
<220> FEATURE:
<223> OTHER INFORMATION: Synthetic Construct

<400> SEQUENCE: 16
caggagcatg ccagaagctg ctatcagaca ctcttt                  36

<210> SEQ ID NO 17
<211> LENGTH: 36
<212> TYPE: DNA
<213> ORGANISM: Artificial Sequence
<220> FEATURE:
<223> OTHER INFORMATION: Synthetic Construct

<400> SEQUENCE: 17
cagcagaatt catgcgagtg ttgaagttcg gcggta                  36

<210> SEQ ID NO 18
<211> LENGTH: 36
<212> TYPE: DNA
<213> ORGANISM: Artificial Sequence
<220> FEATURE:
<223> OTHER INFORMATION: Synthetic Construct
```

```
<400> SEQUENCE: 18
cagagctgca gtccgtccaa atctcgcaac aatcgg                                36

<210> SEQ ID NO 19
<211> LENGTH: 72
<212> TYPE: DNA
<213> ORGANISM: Artificial Sequence
<220> FEATURE:
<223> OTHER INFORMATION: Synthetic Construct

<400> SEQUENCE: 19
atgccacatt cactgttcag caccgatacc gatctcaccg ccgaaaatct gattgcagca      60
ttacacgtct tg                                                          72

<210> SEQ ID NO 20
<211> LENGTH: 71
<212> TYPE: DNA
<213> ORGANISM: Artificial Sequence
<220> FEATURE:
<223> OTHER INFORMATION: Synthetic Construct

<400> SEQUENCE: 20
gttgataagg aacagaaagc ccaccgcccg cagaaatagc ctgtaaatcc cacttaacgg      60
ctgacatggg a                                                           71

<210> SEQ ID NO 21
<211> LENGTH: 77
<212> TYPE: DNA
<213> ORGANISM: Artificial Sequence
<220> FEATURE:
<223> OTHER INFORMATION: Synthetic Construct

<400> SEQUENCE: 21
gtgtgccgga cgagctaccc gccgtcaatt tcttgcgtga agaaaacgtc tttgtgattg      60
cagcattaca cgtcttg                                                     77

<210> SEQ ID NO 22
<211> LENGTH: 71
<212> TYPE: DNA
<213> ORGANISM: Artificial Sequence
<220> FEATURE:
<223> OTHER INFORMATION: Synthetic Construct

<400> SEQUENCE: 22
cgggatggcc cgtcacaaag gcaatgcgct tatctttact ggcaaacaga cacttaacgg      60
ctgacatggg a                                                           71

<210> SEQ ID NO 23
<211> LENGTH: 72
<212> TYPE: DNA
<213> ORGANISM: Artificial Sequence
<220> FEATURE:
<223> OTHER INFORMATION: Synthetic Construct

<400> SEQUENCE: 23
atgaaagcgt tatccaaact gaaagcggaa gagggcatct ggatgaccga gattgcagca      60
ttacacgtct tg                                                          72

<210> SEQ ID NO 24
<211> LENGTH: 71
<212> TYPE: DNA
<213> ORGANISM: Artificial Sequence
```

```
<220> FEATURE:
<223> OTHER INFORMATION: Synthetic Construct

<400> SEQUENCE: 24
atcactttgg tccagtcgat agacatatca gacggcggaa tacccagcat cacttaacgg    60
ctgacatggg a                                                         71

<210> SEQ ID NO 25
<211> LENGTH: 72
<212> TYPE: DNA
<213> ORGANISM: Artificial Sequence
<220> FEATURE:
<223> OTHER INFORMATION: Synthetic Construct

<400> SEQUENCE: 25
tgaaaatgat ttccacgata cagaaaaaag agactgtcat ggtcgcaccc gattgcagca    60
ttacacgtct tg                                                        72

<210> SEQ ID NO 26
<211> LENGTH: 71
<212> TYPE: DNA
<213> ORGANISM: Artificial Sequence
<220> FEATURE:
<223> OTHER INFORMATION: Synthetic Construct

<400> SEQUENCE: 26
atagaaattg cggcaaacgg ttcacggtgc tcatcgaaaa tacacgctgc cacttaacgg    60
ctgacatggg a                                                         71

<210> SEQ ID NO 27
<211> LENGTH: 72
<212> TYPE: DNA
<213> ORGANISM: Artificial Sequence
<220> FEATURE:
<223> OTHER INFORMATION: Synthetic Construct

<400> SEQUENCE: 27
atcgccagcc agtgcacagc tttaagctgc gcggcgcata cgccatgatg gattgcagca    60
ttacacgtct tg                                                        72

<210> SEQ ID NO 28
<211> LENGTH: 71
<212> TYPE: DNA
<213> ORGANISM: Artificial Sequence
<220> FEATURE:
<223> OTHER INFORMATION: Synthetic Construct

<400> SEQUENCE: 28
cccctgctgc tgtgacagtt cgatcgcttt ggctttcgct tcatcaaagt cacttaacgg    60
ctgacatggg a                                                         71

<210> SEQ ID NO 29
<211> LENGTH: 38
<212> TYPE: DNA
<213> ORGANISM: Artificial Sequence
<220> FEATURE:
<223> OTHER INFORMATION: Synthetic Construct

<400> SEQUENCE: 29
gacgggatcc gcaaagcctg tgcgctgatc accgacgg                            38
```

```
<210> SEQ ID NO 30
<211> LENGTH: 38
<212> TYPE: DNA
<213> ORGANISM: Artificial Sequence
<220> FEATURE:
<223> OTHER INFORMATION: Synthetic Construct

<400> SEQUENCE: 30
cacgcctaac cgcgcagaaa aaaacgcgac gccctgcg                              38

<210> SEQ ID NO 31
<211> LENGTH: 38
<212> TYPE: DNA
<213> ORGANISM: Artificial Sequence
<220> FEATURE:
<223> OTHER INFORMATION: Synthetic Construct

<400> SEQUENCE: 31
cgcagggcgt cgcgtttttt tctgcgcggt taggcgtg                              38

<210> SEQ ID NO 32
<211> LENGTH: 40
<212> TYPE: DNA
<213> ORGANISM: Artificial Sequence
<220> FEATURE:
<223> OTHER INFORMATION: Synthetic Construct

<400> SEQUENCE: 32
caggtactgc agaccggaaa gaatatgcgc cagccgttcg                            40

<210> SEQ ID NO 33
<211> LENGTH: 64
<212> TYPE: DNA
<213> ORGANISM: Artificial Sequence
<220> FEATURE:
<223> OTHER INFORMATION: Synthetic Construct

<400> SEQUENCE: 33
atataagctt taccgttcgt atagcataca ttatacgaag ttatctgccc tgaaccgacg      60
accg                                                                  64

<210> SEQ ID NO 34
<211> LENGTH: 65
<212> TYPE: DNA
<213> ORGANISM: Artificial Sequence
<220> FEATURE:
<223> OTHER INFORMATION: Synthetic Construct

<400> SEQUENCE: 34
aattcccggg taccgttcgt ataatgtatg ctatacgaag ttatgcatca cccgacgcac      60
tttgc                                                                 65

<210> SEQ ID NO 35
<211> LENGTH: 71
<212> TYPE: DNA
<213> ORGANISM: Artificial Sequence
<220> FEATURE:
<223> OTHER INFORMATION: Synthetic Construct

<400> SEQUENCE: 35
gcgtaaatca gataccacat ggacgttagg cttgtttggt acggcaatcg taggtgacac      60
tatagaacgc g                                                          71
```

```
<210> SEQ ID NO 36
<211> LENGTH: 70
<212> TYPE: DNA
<213> ORGANISM: Artificial Sequence
<220> FEATURE:
<223> OTHER INFORMATION: Synthetic Construct

<400> SEQUENCE: 36
ccagtgtaat cgcgaacgtt gttttggtac cggtcatgga cgcaaagtgg tagtggatct      60
gatgggtacc                                                            70

<210> SEQ ID NO 37
<211> LENGTH: 70
<212> TYPE: DNA
<213> ORGANISM: Artificial Sequence
<220> FEATURE:
<223> OTHER INFORMATION: Synthetic Construct

<400> SEQUENCE: 37
atgagtactt cagatagcat tgtatccagc cagacaaaac aatcgtcctg gcgtaaatca      60
gataccacat                                                            70

<210> SEQ ID NO 38
<211> LENGTH: 69
<212> TYPE: DNA
<213> ORGANISM: Artificial Sequence
<220> FEATURE:
<223> OTHER INFORMATION: Synthetic Construct

<400> SEQUENCE: 38
gaagaaagat ttgaagatag ccacgagtgc gatgatggaa gccgcatatt ccagtgtaat      60
cgcgaacgt                                                             69

<210> SEQ ID NO 39
<211> LENGTH: 71
<212> TYPE: DNA
<213> ORGANISM: Artificial Sequence
<220> FEATURE:
<223> OTHER INFORMATION: Synthetic Construct

<400> SEQUENCE: 39
ctgcgggcaa ccatgcgcaa ggggtttccc tctcctgcgc gatgctgggt taggtgacac      60
tatagaacgc g                                                          71

<210> SEQ ID NO 40
<211> LENGTH: 65
<212> TYPE: DNA
<213> ORGANISM: Artificial Sequence
<220> FEATURE:
<223> OTHER INFORMATION: Synthetic Construct

<400> SEQUENCE: 40
tctgcgcttt ggcttccgcc atgttggccg gagacagagt aaacaggcag ctaaaggcaa      60
agaac                                                                 65

<210> SEQ ID NO 41
<211> LENGTH: 70
<212> TYPE: DNA
<213> ORGANISM: Artificial Sequence
<220> FEATURE:
<223> OTHER INFORMATION: Synthetic Construct
```

-continued

```
<400> SEQUENCE: 41
attaagttca ctgaccgatg cggaaaaacg caaaggcgtg gtggcctgtt ctgcgggcaa    60
ccatgcgcaa                                                            70

<210> SEQ ID NO 42
<211> LENGTH: 71
<212> TYPE: DNA
<213> ORGANISM: Artificial Sequence
<220> FEATURE:
<223> OTHER INFORMATION: Synthetic Construct

<400> SEQUENCE: 42
ctgcgggcaa ccatgcgcaa ggggtttccc tctcctgcgc gatgctgggt taggtgacac    60
tatagaacgc g                                                          71

<210> SEQ ID NO 43
<211> LENGTH: 66
<212> TYPE: DNA
<213> ORGANISM: Artificial Sequence
<220> FEATURE:
<223> OTHER INFORMATION: Synthetic Construct

<400> SEQUENCE: 43
ggcagctaaa ggcaaagaac atcaccactg caaccatcag catgcttagt ggatctgatg    60
ggtacc                                                                66

<210> SEQ ID NO 44
<211> LENGTH: 61
<212> TYPE: DNA
<213> ORGANISM: Artificial Sequence
<220> FEATURE:
<223> OTHER INFORMATION: Synthetic Construct

<400> SEQUENCE: 44 gccccctatgt gtaacaaata accacactgt gaatgttgtc taggtgacac tatagaacgc    60
g                                                                     61

<210> SEQ ID NO 45
<211> LENGTH: 61
<212> TYPE: DNA
<213> ORGANISM: Artificial Sequence
<220> FEATURE:
<223> OTHER INFORMATION: Synthetic Construct

<400> SEQUENCE: 45 gccccctatgt gtaacaaata accacactgt gaatgttgtc taggtgacac tatagaacgc    60
g                                                                     61

<210> SEQ ID NO 46
<211> LENGTH: 60
<212> TYPE: DNA
<213> ORGANISM: Artificial Sequence
<220> FEATURE:
<223> OTHER INFORMATION: Synthetic Construct

<400> SEQUENCE: 46
tcacgacagt aaccgcacct acactgtcat gacattgctc gccccctatgt gtaacaaata   60

<210> SEQ ID NO 47
<211> LENGTH: 60
<212> TYPE: DNA
<213> ORGANISM: Artificial Sequence
```

```
<220> FEATURE:
<223> OTHER INFORMATION: Synthetic Construct

<400> SEQUENCE: 47
tcacgacagt aaccgcacct acactgtcat gacattgctc gccctatgt gtaacaaata        60

<210> SEQ ID NO 48
<211> LENGTH: 81
<212> TYPE: DNA
<213> ORGANISM: Artificial Sequence
<220> FEATURE:
<223> OTHER INFORMATION: Synthetic Construct

<400> SEQUENCE: 48
cgatgttggc aggaatggtg tgtttgtgaa tttggctcat ggtctgtttc ctgtgtgaaa        60
ttgttatccg ctcacaattc c                                                  81

<210> SEQ ID NO 49
<211> LENGTH: 60
<212> TYPE: DNA
<213> ORGANISM: Artificial Sequence
<220> FEATURE:
<223> OTHER INFORMATION: Synthetic Construct

<400> SEQUENCE: 49
cgaattgcgc cattgttgca atggcggttt ttattgtttt tcacgacagt aaccgcacct        60

<210> SEQ ID NO 50
<211> LENGTH: 70
<212> TYPE: DNA
<213> ORGANISM: Artificial Sequence
<220> FEATURE:
<223> OTHER INFORMATION: Synthetic Construct

<400> SEQUENCE: 50
ttgttgatac atcgcctcgt actgctgagg gtttatcagg caacggtctg cgatgttggc        60
aggaatggtg                                                               70

<210> SEQ ID NO 51
<211> LENGTH: 71
<212> TYPE: DNA
<213> ORGANISM: Artificial Sequence
<220> FEATURE:
<223> OTHER INFORMATION: Synthetic Construct

<400> SEQUENCE: 51
atggagatgt tgtctggagc cgagatggtc gtccgatcgc ttatcgatca taggtgacac        60
tatagaacgc g                                                             71

<210> SEQ ID NO 52
<211> LENGTH: 70
<212> TYPE: DNA
<213> ORGANISM: Artificial Sequence
<220> FEATURE:
<223> OTHER INFORMATION: Synthetic Construct

<400> SEQUENCE: 52
tcaacgcatt attttatcgc cgcgcgaaag tccgaccaca ccagagcgag tagtggatct        60
gatgggtacc                                                               70

<210> SEQ ID NO 53
<211> LENGTH: 71
<212> TYPE: DNA
<213> ORGANISM: Artificial Sequence
```

<220> FEATURE:
<223> OTHER INFORMATION: Synthetic Construct

<400> SEQUENCE: 53
atggcaagtt cgggcacaac atcgacgcgt aagcgcttta ccggcgcaga taggtgacac    60
tatagaacgc g    71

<210> SEQ ID NO 54
<211> LENGTH: 71
<212> TYPE: DNA
<213> ORGANISM: Artificial Sequence
<220> FEATURE:
<223> OTHER INFORMATION: Synthetic Construct

<400> SEQUENCE: 54
tttactgaaa aaacaccgcg atcttgttaa acatcgtcgg atcggactga ttagtggatc    60
tgatgggtac c    71

<210> SEQ ID NO 55
<211> LENGTH: 30
<212> TYPE: DNA
<213> ORGANISM: Artificial Sequence
<220> FEATURE:
<223> OTHER INFORMATION: Synthetic Construct

<400> SEQUENCE: 55
atacggatcc tggtgacctg atcgctatcg    30

<210> SEQ ID NO 56
<211> LENGTH: 54
<212> TYPE: DNA
<213> ORGANISM: Artificial Sequence
<220> FEATURE:
<223> OTHER INFORMATION: Synthetic Construct

<400> SEQUENCE: 56
tgttggcgaa gcgcagaaac gcgcccggtg attccgggaa ttcgaagctg taga    54

<210> SEQ ID NO 57
<211> LENGTH: 54
<212> TYPE: DNA
<213> ORGANISM: Artificial Sequence
<220> FEATURE:
<223> OTHER INFORMATION: Synthetic Construct

<400> SEQUENCE: 57
tctacagctt cgaattcccg gaatcaccgg gcgcgtttct gcgcttcgcc aaca    54

<210> SEQ ID NO 58
<211> LENGTH: 30
<212> TYPE: DNA
<213> ORGANISM: Artificial Sequence
<220> FEATURE:
<223> OTHER INFORMATION: Synthetic Construct

<400> SEQUENCE: 58
agtcctgcag gtggtttcga cgcaataaaa    30

<210> SEQ ID NO 59
<211> LENGTH: 81
<212> TYPE: DNA
<213> ORGANISM: Artificial Sequence
<220> FEATURE:
<223> OTHER INFORMATION: Synthetic Construct

<400> SEQUENCE: 59
ccgaaccgtg gcattcagtt acaggtaagc gatgccgaac tggcggcgcg cgaatatttg    60
attgcagcat tacacgtctt g    81

<210> SEQ ID NO 60
<211> LENGTH: 79
<212> TYPE: DNA
<213> ORGANISM: Artificial Sequence
<220> FEATURE:
<223> OTHER INFORMATION: Synthetic Construct

<400> SEQUENCE: 60
cttaaatatt cggcaccttc cggagcaccg gacaggggtt gcgagtcagc cgtcgtggcc    60
acttaacggc tgacatggg    79

<210> SEQ ID NO 61
<211> LENGTH: 30
<212> TYPE: DNA
<213> ORGANISM: Artificial Sequence
<220> FEATURE:
<223> OTHER INFORMATION: Synthetic Construct

<400> SEQUENCE: 61
gccatctaga atgaaaacaa aattgatgac    30

<210> SEQ ID NO 62
<211> LENGTH: 30
<212> TYPE: DNA
<213> ORGANISM: Artificial Sequence
<220> FEATURE:
<223> OTHER INFORMATION: Synthetic Construct

<400> SEQUENCE: 62
tattgcatgc tcagaacagc gttaaaccaa    30

<210> SEQ ID NO 63
<211> LENGTH: 30
<212> TYPE: DNA
<213> ORGANISM: Artificial Sequence
<220> FEATURE:
<223> OTHER INFORMATION: Synthetic Construct

<400> SEQUENCE: 63
actcgagctc gagacagaca ctgggagtaa    30

<210> SEQ ID NO 64
<211> LENGTH: 30
<212> TYPE: DNA
<213> ORGANISM: Artificial Sequence
<220> FEATURE:
<223> OTHER INFORMATION: Synthetic Construct

<400> SEQUENCE: 64
tacgtctaga ttaaccccccc agtttcgatt    30

<210> SEQ ID NO 65
<211> LENGTH: 30
<212> TYPE: DNA
<213> ORGANISM: Artificial Sequence
<220> FEATURE:
<223> OTHER INFORMATION: Synthetic Construct

<400> SEQUENCE: 65
tacgtctaga ttaaccccccc agtttcgatt    30

```
<210> SEQ ID NO 66
<211> LENGTH: 41
<212> TYPE: DNA
<213> ORGANISM: Artificial Sequence
<220> FEATURE:
<223> OTHER INFORMATION: Synthetic Construct

<400> SEQUENCE: 66
gtgctctaga aggcctgatc agctagctgt ttcctgtgtg a                    41

<210> SEQ ID NO 67
<211> LENGTH: 30
<212> TYPE: DNA
<213> ORGANISM: Artificial Sequence
<220> FEATURE:
<223> OTHER INFORMATION: Synthetic Construct

<400> SEQUENCE: 67
tatagaattc atggctgtta ctaatgtcgc                                 30

<210> SEQ ID NO 68
<211> LENGTH: 30
<212> TYPE: DNA
<213> ORGANISM: Artificial Sequence
<220> FEATURE:
<223> OTHER INFORMATION: Synthetic Construct

<400> SEQUENCE: 68
tattgagctc ttaagcggat tttttcgctt                                 30

<210> SEQ ID NO 69
<211> LENGTH: 30
<212> TYPE: DNA
<213> ORGANISM: Artificial Sequence
<220> FEATURE:
<223> OTHER INFORMATION: Synthetic Construct

<400> SEQUENCE: 69
gttgcccggg atgcgagtgt tgaagttcgg                                 30

<210> SEQ ID NO 70
<211> LENGTH: 31
<212> TYPE: DNA
<213> ORGANISM: Artificial Sequence
<220> FEATURE:
<223> OTHER INFORMATION: Synthetic Construct

<400> SEQUENCE: 70
gcgtcaagct tcggcggttg ttattctccg c                               31
```